United States Patent [19]

Fuller et al.

[11] Patent Number: 5,250,571
[45] Date of Patent: Oct. 5, 1993

[54] (S)-NORFLUOXETINE IN METHOD OF INHIBITING SEROTONIN UPTAKE

[75] Inventors: Ray W. Fuller; David Mitchell, both of Indianapolis; David W. Robertson, Greenwood; Gregory A. Stephenson, Anderson; David T. Wong, Indianapolis, all of Ind.

[73] Assignee: Eli Lilly and Company, Indianapolis, Ind.

[21] Appl. No.: 873,520

[22] Filed: Apr. 21, 1992

Related U.S. Application Data

[63] Continuation of Ser. No. 615,201, Nov. 19, 1990, abandoned, which is a continuation-in-part of Ser. No. 486,478, Feb. 28, 1990, abandoned, which is a continuation-in-part of Ser. No. 412,687, Sep. 26, 1989, abandoned, which is a continuation-in-part of Ser. No. 270,177, Nov. 14, 1988, abandoned.

[51] Int. Cl.$^5$ ............................................. A61K 31/165
[52] U.S. Cl. ..................................... 514/651; 514/811; 514/813; 514/909; 514/910; 564/304; 564/347
[58] Field of Search ................ 564/304, 347; 514/651, 514/811, 813, 909, 910

[56] References Cited

U.S. PATENT DOCUMENTS

| | | | |
|---|---|---|---|
| 4,018,895 | 4/1977 | Molloy et al. | 514/651 |
| 4,194,009 | 5/1980 | Molloy et al. | 514/651 |
| 4,313,896 | 2/1982 | Molloy et al. | 260/501.18 |
| 4,314,081 | 2/1982 | Molloy et al. | 564/347 |
| 4,584,404 | 4/1986 | Molloy et al. | 564/347 |
| 4,626,549 | 12/1986 | Molloy et al. | 514/651 |

FOREIGN PATENT DOCUMENTS 369685 5/1990 European Pat. Off.

OTHER PUBLICATIONS

Wong, et al., *Acta Pharm. Nord.*, 2 (3), 771 (1990).
Robertson et al., *J. Med. Chem.*, 31, 1412 (1988).
Wong et al., *Drug Development Research*, 6, 397 (1985).
Fuller et al., *Pharmacology Biochemistry and Behavior*, 24, 281 (1986).
Nash et al., *Clin. Chem.*, 28(10), 2100 (1982).
Aronoff et al., *Clin. Pharmacol. Ther.*, 36(1), 138 (1984).

*Primary Examiner*—Richard L. Raymond
*Attorney, Agent, or Firm*—Joseph A. Jones; Leroy Whitaker; Robert A. Conrad

[57] ABSTRACT

The present invention provides (S)-norfluoxetine and pharmaceutically acceptable salts thereof capable of inhibiting the uptake of serotonin.

25 Claims, No Drawings

(S)-NORFLUOXETINE IN METHOD OF INHIBITING SEROTONIN UPTAKE

CROSS REFERENCE

This application is a continuation of application Ser. No. 07/615,201, filed on Nov. 19, 1990, and now abandoned, which was a continuation-in-part of application Ser. No. 07/486,478, filed Feb. 28, 1990, now abandoned, which was in turn a continuation-in-part of application Ser. No. 07/412,687, filed Sep. 26, 1989, now abandoned, which was a continuation-in-part of application Ser. No. 07/270,177, filed Nov. 14, 1988, now abandoned.

BACKGROUND OF THE INVENTION

During the past decade, the relationship between monoamine uptake and a variety of diseases and conditions has been appreciated and investigated. For example, the hydrochloride salt of fluoxetine (dlN-methyl-3-[4-(trifluoromethyl)phenoxy]-3-phenylpropylamine) is a selective serotonin (5-hydroxytryptamine) uptake inhibitor. Fluoxetine hydrochloride is marketed under the trademark PROZAC ® for the treatment of depression. This compound is among many taught in U.S. Pat. Nos. 4,018,895, 4,194,009, and 4,314,081 as being potent, selective blockers of serotonin uptake.

Fluoxetine is a racemate of the two enantiomeric forms. The biological and pharmacological activity of each enantiomer has been found to be essentially the same; see, Robertson et al., *J. Med. Chem.*, 31, 1412 (1988) and references cited therein.

Norfluoxetine [3-(4-trifluoromethylphenoxy)3-phenylpropylamine] is a metabolite of fluoxetine and is known to block monoamine uptake, especially serotonin. See U.S. Pat. No. 4,313,896. Norfluoxetine has only been evaluated as the racemate, and since it is a metabolite of fluoxetine, it is believed that this compound contributes in part to the biological activity seen upon administration of fluoxetine. Since the eudismic ratio for norfluoxetine, i.e., the ratio of affinities or activities of its two enantiomers, is approximately unity, conventional wisdom would suggest that the individual enantiomers of norfluoxetine would similarly have equivalent activities. We have unexpectedly discovered that the (S)-enantiomer of norfluoxetine is substantially more active than its (R)-optical antipode.

SUMMARY OF THE INVENTION

This invention provides the compound (S)norfluoxetine and pharmaceutically acceptable salts and solvates thereof. Also provided is a method for inhibiting serotonin uptake in mammals which comprises administering to a mammal requiring increased neurotransmission of serotonin an effective amount of (S)norfluoxetine or a pharmaceutically acceptable salt or solvate thereof. Further provided by this invention are pharmaceutical formulations comprising (S)-norfluoxetine, or a pharmaceutically acceptable salt or solvate thereof, in combination with one or more pharmaceutically acceptable carriers, diluents, or excipients therefor. Three polymorphs of (S)-norfluoxetine hydrochloride are also provided.

DETAILED DESCRIPTION AND PREFERRED EMBODIMENT

This invention includes the pharmaceutically acceptable acid addition salts of (S)-norfluoxetine. Since (S)-norfluoxetine is an amine, it is basic in nature and accordingly reacts with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, $\beta$-hydroxybutyrate, glycollate, maleate, tartrate, methanesulfonate, propanesulfonates, naphthalene-1-sulfonate, naphthalene-2-sulfonate, mandelate, hippurate, gluconate, lactobionate, and the like salts. Preferred pharmaceutically acceptable acid addition salts include those formed with mineral acids such as hydrochloric acid and hydrobromic acid, and those formed with organic acids such as fumaric acid and maleic acid.

The pharmaceutically acceptable acid addition salts of (S)-norfluoxetine can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent. The hydrates are particularly useful, especially those of the maleate salt of (S)-norfluoxetine. (S)-Norfluoxetine maleate hemihydrate is particularly useful because of its crystalline properties.

(S)-Norfluoxetine can be prepared by any of a number of methods generally known in the art. For example, there are several methods provided in the literature for making the racemate of norfluoxetine, see U.S. Pat. No. 4,313,896. The racemate of norfluoxetine in turn can be resolved into its (S) and (R) components by standard methods. In particular, norfluoxetine can be reacted with an enantiomerically pure chiral derivatizing agent, resolved on the basis of the different physicochemical properties of the diastereomeric derivatives, and then converted to the two separate enantiomers of norfluoxetine. One particularly preferred method of accomplishing this derivatization is analogous to that described in Robertson et al., *J. Med. Chem.*, 31, 1412 (1988), wherein fluoxetine was reacted with an optically active form of 1-(1-naphthyl)ethyl isocyanate to form a urea derivative of fluoxetine. A similar mixture of norfluoxetine diastereomeric ureas can be separated through high pressure liquid chromatography into the individual diastereomers. Each individual diastereomer, in turn, can then be hydrolyzed to the individual enantiomers of norfluoxetine.

A preferred method of preparing (S)-norfluoxetine is similar to that labeled Scheme I in the Robertson et al. reference. (S)-(−)-3-Chloro-1-phenylpropanol (II) is either commercially available or can be prepared by chiral reduction of 3-chloropropiophenone. II can be transformed into (S)-3-amino-1-phenylpropanol (III). Although a number of routes to convert the chloride intermediate to the amino compound are available, the preferred method is the transformation of the chloride to an intermediate N-substituted phthalimide which can be transformed to the desired primary amino intermediate III. This reaction sequence is a Gabriel synthesis wherein the potassium salt of phthalimide is reacted with (S)-(−)-3-chloro-1-phenylpropanol, preferably in the presence of a nonreactive solvent such as dimethylformamide or especially dimethylsulfoxide, to prepare the (S)-3-phthalimido-1-phenylpropanol intermediate. The phthalimido intermediate may be hydrolyzed to provide the desired amino intermediate III. However, to prevent the possible racemization of the intermediate, the phthalimide intermediate is preferably treated with hydrazine in a nonreactive solvent such as ethanol to provide the desired (S)-3-amino-1-phenylpropanol intermediate III. This latter compound can then be reacted with sodium hydride in dimethylacetamide or some other nonreactive solvent, preferably dimethylsulfoxide, to generate the alkoxide which, upon treatment with 4-chloro or 4-fluoro-benzotrifluoride, leads to a facile nucleophilic aromatic substitution to provide (S)-norfluoxetine.

Alternatively, commercially available (R)-3-phenyloxiranemethanol ((2R,3R)-(+)-3-phenylglycidol) can be treated with a reducing agent such as sodium bis(2-methoxyethoxy)aluminum hydride in a non-reactive solvent such as dimethoxyethane to provide (S)-1-phenyl1,3-propanediol. The primary alcohol group of this diol intermediate is then converted into a good leaving group which can be displaced with ammonia. For example (S)-1-phenyl-1,3-propanediol is treated with a nonreactive base in an inert solvent, such as the use of triethylamine in tetrahydrofuran or dichloromethane. Treatment with a sulfonyl chloride, such as methanesulfonyl chloride, p-toluenesulfonyl chloride, p-chlorophenylsulfonyl chloride, or preferably p-bromophenylsulfonyl chloride, provides the corresponding sulfonate ester (eg, the mesylate, tosylate, p-chlorophenylsulfonate, or p-bromophenylsulfonate, respectively). When any of these sulfonate esters are treated with ammonia, for example, gaseous ammonia dissolved in an alcohol, such as methanol, under pressure, for example at 60 p.s.i., provides the corresponding amine sulfonate salt which can be converted to III upon treatment with base. This sequence is preferred for large scale preparation.

A less direct way of preparing III involves taking a sulfonate ester (as described in the preceding paragraph) of commercially available (R)-1-phenyl-1,2-ethanediol, protecting the remaining alcohol with, for example, a silyl group, such as reacting the alcohol with t-butyldimethylsilyl chloride in the presence of a non-reactive base, such as imidazole, in an inert solvent such as dimethylformamide. This protected sulfonate ester can then be reacted with cyanide, such as with potassium or sodium cyanide, in a non-reactive solvent, such as dimethylformamide or dimethylsulfoxide, at temperature of about 50°–100° C., to give silyl protected (R)-3-phenyl-3-hydroxypropionitrile, which can be reduced (eg, a borane or aluminum hydride reagent, particularly borane-tetrahydrofuran complex in tetrahydrofuran) and hydrolyzed (eg, treatment with 3 N hydrochloric acid) to give III. This procedure is particularly useful for preparing radiolabelled III, such as by using $^{14}C$-labelled sodium cyanide.

The pharmaceutically acceptable acid addition salts of the invention are typically formed by reacting (S)-norfluoxetine with an equimolar or excess amount of acid. The reactants are generally combined in a mutual solvent such as diethyl ether or benzene, and the salt normally precipitates out of solution within about one minute to 10 days, and can be isolated by filtration.

The following example further illustrates the compound of the present invention and methods for its preparation. The example is not intended to be limiting to the scope of the invention in any respect and should not be so construed.

EXAMPLE 1

(S)-Norfluoxetine

A. Preparation of (S)-3-phthalimido-1-phenylpropanol.

To a solution of 470 mg of (S)-(-)-3-chloro-1phenylpropanol in 4 ml of dimethylformamide were added 612 mg of potassium phthalimide in 4 ml of dimethylformamide. The mixture was heated at 100° C. for 6 hours, allowed to cool to room temperature, and stirred overnight. The mixture was filtered, the filtrate diluted with water, and the solution extracted with ethyl acetate. The organic layer was washed once with water, once with 0.2 N sodium hydroxide, once again with water, and once with a saturated solution of sodium chloride, dried over sodium sulfate, and concentrated in vacuo to provide 730 mg of an opaque oil that solidified. Crystallization from ethyl acetate/hexanes provided 350 mg of the title intermediate as a white powder, m.p. 80°–82.5° C.

Analysis for $C_{17}H_{15}NO_3$:
Calc.: C, 72.58; H, 5.38; N, 4.98;
Found: C, 72.57; H, 5.40; N, 4.96.

B. Preparation of (S)-3-amino-1-phenyl-1-propanol.

To a solution of 4.04 g of (S)-3-phthalimido1-phenyl-1-propanol in 100 ml of ethanol was added 2.5 ml of anhydrous hydrazine. The mixture was heated to reflux under a nitrogen atmosphere for 3.5 hours, cooled to room temperature, and allowed to stir overnight. The resulting precipitate was removed by filtration and the filtrate concentrated in vacuo. The resulting oil was treated with diethyl ether and 25 ml of 5 N sodium hydroxide. The layers were separated, and the organic layer was dried over sodium sulfate and concentrated in vacuo to provide 1.92 g of an opaque oil. Two hundred milligrams of this oil was treated with oxalic acid in ethyl acetate and crystallized from ethyl acetate/methanol to provide 210 mg of the title intermediate as the oxalate salt, m.p. 161°–162° C.

Analysis of the oxalate salt: $C_{11}H_{15}NO_5$:
Calc.: C, 54.77; H, 6.27; N, 5.81;
Found: C, 54.96; H, 6.15; N, 5.79.

C. Preparation of (S)-norfluoxetine.

To a slurry of 484 mg of 60% sodium hydride in oil in 10 ml of dimethylacetamide were added 1.74 g of (S)-3-amino-1-phenyl-1-propanol in 40 ml of dimethylacetamide. The mixture was heated at 70° C. for 10 minutes. 4-Fluorobenzotrifluoride (1.54 ml) was added to the reaction mixture and the solution heated at 100° C. for 3 hours. The mixture was poured into ice water and extracted into diethyl ether. The organic extract was washed three times with water, once with a saturated sodium chloride solution, dried over sodium sulfate and concentrated in vacuo to provide 2.96 g of a yellow oil. The oil was purified by high pressure liquid chromatography over silica gel eluting with a gradient of methylene chloride to 10% methanol in methylene chloride to which 0.5% of ammonium hydroxide had been added. The desired fractions were combined and concentrated in vacuo to yield 1.5 g of the title product as an amber oil. The residue was dissolved in ethyl acetate and a solution of 451 mg of oxalic acid in ethyl acetate was added. The resulting precipitate was crystallized from ethyl acetate/methanol to provide 1.67 g of the desired title product as the oxalate salt, m.p. 148°–150° C.

Analysis for $C_{18}H_{18}F_3NO_5$ ((S)-norfluoxetine oxalate):
Calc.: C, 56.11; H, 4.71; N, 3.64;
Found: C, 56.05; H, 4.59; N, 3.59.

In the same way were prepared the following salts employing the appropriate acid:

(S)-norfluoxetine hydrochloride (from diethyl ether/hexanes), m.p. 128°–130° C.
Analysis for $C_{16}H_{16}F_3N \cdot HCl$:
Calc.: C, 57.93; H, 5.17; N, 4.22;
Found: C, 57.86; H, 4.94; N, 4.15.

(S)-norfluoxetine fumarate (from ethyl acetate/methanol), m.p. 156°–157° C.
Analysis for $C_{20}H_{20}F_3NO_5$:
Calc.: C, 58.39; H, 4.90; N, 3.41;
Found: C, 58.63; H, 4.90; N, 3.57.

(S)-norfluoxetine maleate hemihydrate, m.p. 94°–96° C. (prepared in and crystallized out of diethyl ether).
Analysis for $C_{20}H_{20}F_3NO_5$ (block dried):
Calc.: C, 58.39; H, 4.90; N, 3.41;
Found: C, 58.18; H, 4.76; N, 3.50.

(S)-norfluoxetine 2,3:4,6-di-O-isopropylidene-2keto-L-gulonate (from ethyl acetate/methanol), m.p. 219°–221.5° C.
Analysis for $C_{28}H_{34}F_3NO_8$:
Calc.: C, 59.05; H, 6.02; N, 2.46;
Found: C, 59.20; H, 5.75; N, 2.43.

(S)-norfluoxetine 2-napsylate (from ethyl acetate/methanol), m.p. 145°–148° C.
Analysis for $C_{26}H_{24}F_3NO_4S$:
Calc.: C, 62.02; H, 4.80; N, 2.78;
Found: C, 62.13; H, 4.91; N, 2.90.

(S)-norfluoxetine L-tartrate (from ethyl acetate/methanol), m.p. 141°–146° C.
Analysis for $C_{20}H_{22}F_3NO_7$:
Calc.: C, 53.94; H, 4.98; N, 3.14;
Found: C, 54.22; H, 5.09; N, 2.99.

(S)-norfluoxetine D-tartrate (from ethyl acetate then isopropyl alcohol), m.p. 152°–153.5° C.
Analysis for $C_{20}H_{22}F_3NO_7$:
Calc.: C, 53.94; H, 4.98; N, 3.14;
Found: C, 54.22; H, 5.09; N, 2.99.

(S)-norfluoxetine L-malate (from ethyl acetate/methanol), m.p. 146°–147.5° C.;
Analysis for: $C_{20}H_{22}F_3NO_6$:
Calc.: C, 55.94; H, 5.16; N, 3.26;
Found: C, 56.23; H, 5.14; N, 3.27.

(S)-norfluoxetine succinate (from ethyl acetate/methanol), m.p. 131°–132° C.
Analysis for $C_{20}H_{22}F_3NO_5$:
Calc.: C, 58.11; H, 5.36; N, 3.39;
Found: C, 57.86; H, 5.30; N, 3.41.

(S)-norfluoxetine tosylate (from diethyl ether/hexane), m.p. 116°–118° C.
Analysis for $C_{23}H_{24}F_3NO_4S$:
Calc.: C, 59.09; H, 5.17; N, 3.00;
Found: C, 59.34; H, 4.93; N, 3.04.

(S)-norfluoxetine hemi-L-tartrate (from ethyl acetate), m.p. 136°–138.5° C.
Analysis for equivalent of $C_{18}H_{19}F_3NO_4$:
Calc.: C, 58.38; H, 5.17; N, 3.78;
Found: C, 58.16; H, 5.08; N, 3.70.

The above maleate hemihydrate had been crystallized from diethyl ether and was found to contain 2.2% of water by thermogravimetric analysis, prior to block drying.

Crystallization of the (S)-norfluoxetine maleate hemihydrate from water provided crystalline (S)-norfluoxetine maleate hydrate (1:0.85), m.p. 97°–101° C., calculated to have 3.6% water by thermogravimetric analysis.

Drying the hemihydrate at 45° C. for one hour in a vacuum oven provided anhydrous (S)-norfluoxetine maleate, m.p. 96°–97° C., thermogravimetric analysis indicating water in the amount of 0.02%.

On standing in the dry state, it was determined that the maleate salt undergoes a reaction to form a 1,4-maleate adduct.

According to the same procedure described above beginning with (R)-(+)-3-chloro-1-phenyl-1-propanol, (R)-norfluoxetine was prepared. The maleate salt of (R)-norfluoxetine had a melting point of 95°–97° C.

The aforementioned (S)-norfluoxetine hydrochloride was prepared by dissolving the free base material in diethyl ether, bubbling in hydrogen chloride gas, adding hexanes, and cooling. X-ray powder diffraction analysis determined that such material was either amorphous or a poorly defined mixture of crystalline forms and amorphous material. The use of concentrated hydrochloric acid in ether and attempting to crystallize from diethyl ether/cyclohexane provided the same result. However, it was observed the use of ammonium chloride or concentrated hydrochloric acid with certain solvent systems can produce one of three polymorphs of (S)-norfluoxetine hydrochloride. Whether or which polymorph is formed is influenced by the choice of solvent(s) employed.

For example, when (S)-norfluoxetine hydrochloride is dissolved in a mixture of a wet ether (i.e., an ether such as diethyl ether or preferably t-butyl methyl ether which is shaken with water and the layers separated before use) and either petroleum ether or heptane, crystalline (S)-norfluoxetine hydrochloride designated Form 1 is obtained, m.p. approximately 130° C., with the following x-ray powder diffraction pattern (Cu/K alpha radiation wavelength =1.5418 Angstroms):

| (S)-Norfluoxetine Hydrochloride Form 1 | |
|---|---|
| Interplanar Spacing d (Å) | Intensity Ratio $I/I_o$ |
| 16.83 | 0.15 |
| 11.89 | 0.19 |
| 10.63 | 0.03 |
| 7.51 | 0.10 |
| 6.05 | 0.03 |
| 5.95 | 0.07 |
| 5.69 | 0.30 |
| 5.60 | 0.02 |
| 5.39 | 0.18 |
| 5.30 | 0.03 |
| 5.13 | 0.10 |
| 4.91 | 0.43 |
| 4.76 | 0.05 |
| 4.67 | 0.05 |
| 4.54 | 0.13 |
| 4.38 | 0.12 |

| (S)-Norfluoxetine Hydrochloride Form 1 | |
| --- | --- |
| Interplanar Spacing d (Å) | Intensity Ratio $I/I_o$ |
| 4.20 | 1.00 |
| 4.11 | 0.13 |
| 4.08 | 0.20 |
| 3.96 | 0.10 |
| 3.89 | 0.05 |
| 3.76 | 0.56 |
| 3.69 | 0.05 |
| 3.53 | 0.06 |
| 3.45 | 0.18 |
| 3.36 | 0.21 |
| 3.30 | 0.05 |
| 3.19 | 0.04 |
| 3.12 | 0.03 |
| 3.06 | 0.04 |
| 2.94 | 0.08 |
| 2.77 | 0.05 |
| 2.61 | 0.04 |
| 2.57 | 0.04 |
| 2.49 | 0.01 |
| 2.36 | 0.04 |
| 2.13 | 0.03 |
| 2.06 | 0.02 |
| 1.62 | 0.01 |

Form 1 appears to be the most stable form of all those discovered. Form 1 can be prepared by recrystallizing other forms (as described below), or poorly defined or amorphous hydrochloride salt from wet ether/petroleum ether. Form 1 is also, and preferably, obtained by crystallization of non-Form 1 (S)-norfluoxetine hydrochloride from ethyl acetate/heptane. Form 1 is also formed from Form 2 on prolonged standing.

Crystalline (S)-norfluoxetine hydrochloride designated Form 2 is obtained in the same manner as described above when the solvent combination tetrahydrofuran/heptane or ethyl acetate/cyclohexane is used to prepare or recrystallize the product. Although the melting point of Form 2 appears to be 130° C., the melt which is being observed is actually that of Form 1. During the melting point determination, there is a solid state transition of Form 2 into Form 1. The transition is fast at elevated temperatures and occurs more slowly at room temperature. Form 2 has the following x-ray pattern:

| (S)-Norfluoxetine Hydrochloride Form 2 | |
| --- | --- |
| Interplanar Spacing d (Å) | Intensity Ratio $I/I_o$ |
| 17.67 | 0.68 |
| 15.65 | 0.23 |
| 12.04 | 0.14 |
| 11.27 | 0.39 |
| 8.86 | 0.12 |
| 7.47 | 0.13 |
| 7.23 | 0.34 |
| 6.01 | 0.38 |
| 5.70 | 0.27 |
| 5.39 | 0.47 |
| 5.22 | 0.29 |
| 4.91 | 0.69 |
| 4.84 | 0.43 |
| 4.55 | 0.22 |
| 4.32 | 1.00 |
| 4.20 | 0.45 |
| 3.94 | 0.96 |
| 3.85 | 0.68 |
| 3.76 | 0.22 |
| 3.71 | 0.20 |
| 3.53 | 0.87 |
| 3.45 | 0.30 |
| 3.30 | 0.33 |
| 3.14 | 0.16 |
| 3.07 | 0.31 |
| 2.94 | 0.22 |
| 2.32 | 0.19 |
| 2.20 | 0.13 |
| 2.02 | 0.02 |

A third form of (S)-norfluoxetine hydrochloride, designated as Form 3, is produced when prepared or crystallized from toluene, toluene/heptane, or tetrahydrofuran/heptane. However, the preferred method of preparing Form 3 is that wherein one part of (S)-norfluoxetine hydrochloride is crystallized from 2.5 parts of ethyl acetate and 10 parts of heptane. Thus, 40 grams of (S)-norfluoxetine hydrochloride were dissolved in 100 mL of ethyl acetate. The solution was heated to 75°-80° C. Heptane (400 mL) was heated to 90° C. and added to the (S)-norfluoxetine hydrochloride/ethyl acetate solution. The solution mixture was allowed to cool and the resulting white crystals were recovered by filtration and washed within fresh solvent mixture to afford the Form 3 product in 68% yield. Form 3 has the following x-ray pattern:

| (S)-Norfluoxetine Hydrochloride Form 3 | |
| --- | --- |
| Interplanar Spacing d (Å) | Intensity Ratio $I/I_o$ |
| 15.49 | 0.36 |
| 14.28 | 0.01 |
| 11.36 | 0.03 |
| 9.25 | 0.03 |
| 8.79 | 0.09 |
| 7.18 | 0.10 |
| 6.70 | 0.02 |
| 6.04 | 0.23 |
| 5.92 | 0.10 |
| 5.84 | 0.05 |
| 5.68 | 0.36 |
| 5.58 | 0.08 |
| 5.49 | 0.11 |
| 5.26 | 0.08 |
| 5.19 | 0.14 |
| 4.89 | 0.12 |
| 4.79 | 0.12 |
| 4.64 | 1.00 |
| 4.57 | 0.71 |
| 4.26 | 0.03 |
| 4.17 | 0.14 |
| 4.04 | 0.06 |
| 3.84 | 0.17 |
| 3.78 | 0.22 |
| 3.76 | 0.35 |
| 3.68 | 0.20 |
| 3.60 | 0.35 |
| 3.46 | 0.10 |
| 3.35 | 0.11 |
| 3.30 | 0.10 |
| 3.25 | 0.04 |
| 3.10 | 0.04 |
| 3.02 | 0.03 |
| 2.97 | 0.04 |
| 2.94 | 0.05 |
| 2.84 | 0.08 |
| 2.60 | 0.04 |

As will be appreciated by these skilled in the art, the precise values of interplanar spacing and intensity ratios may vary slightly depending upon compound or crystalline purity, the instrument used to make such an analysis, or operator variables. This invention covers each of the three polymorphs having substantially the same respective values as noted above.

The preferred way of making (S)-norfluoxetine hydrochloride comprises allowing (S)-3-amino-1-phenylpropanol and 4-chlorobenzotrifluoride to react as described above in the presence of sodium hydride and dimethylsulfoxide, preferably by heating at about 85°–90° C. for approximately one hour. The reaction is cooled and quenched with water, then extracted with toluene. The toluene extract is filtered through diatomaceous earth and treated with heptane. Gaseous hydrogen chloride gas is bubbled carefully into the solution and the resulting "crude" (S)-norfluoxetine hydrochloride, a poorly defined mixture of Forms 2 and 3, is recovered by filtration. This "crude" material is then recrystallized from ethyl acetate/heptane to provide (S)-norfluoxetine hydrochloride Form 1.

(S)-Norfluoxetine is useful for inhibiting the uptake of serotonin. Therefore, another embodiment of the present invention is a method for inhibiting serotonin uptake in mammals which comprises administering to a mammal requiring increased neurotransmission of serotonin a pharmaceutically effective amount of (S)-norfluoxetine or a pharmaceutically acceptable salt thereof.

The term "pharmaceutically effective amount", as used herein, represents an amount of (S)-norfluoxetine which is capable of inhibiting serotonin uptake. The particular dose of compound administered according to this invention will, of course, be determined by the particular circumstances surrounding the case, including the route of administration, the particular condition being treated, and similar considerations. (S)-Norfluoxetine can be administered by a variety of routes including the oral, rectal, transdermal, subcutaneous, intravenous, intramuscular or intranasal routes. A typical daily dose will contain from about 0.01 mg/kg to about 20 mg/kg of (S)-norfluoxetine. Preferred daily doses will be about 0.05 to about 10 mg/kg, ideally about 0.1 to about 5 mg/kg.

(S)-Norfluoxetine has the ability to treat a variety of disorders in mammals influenced by serotonergic systems such as obesity, bulimia, obsessivecompulsive disorders, depression, aggression, alcoholism, pain, premenstrual syndrome (PMS), loss of memory, anxiety, panic attack, smoking, symptoms associated with nicotine withdrawal, sleep disorders such as narcolepsy or sleep apnea, urinary incontinence, substance abuse (eg, cocaine, heroin, amphetamines, etc.), dementia, emotional disturbance associated with Alzheimer's Disease, and migraine. The compound can be used as an aid in increasing the rate of recanalization following thrombolytic or angioplasty therapy, and can be used to prevent restenosis or vasospasm following thrombolysis or angioplasty therapy. (S)-Norfluoxetine also has little effect on metabolism of concurrently administered drugs such as barbiturates or tricyclic antidepressants, unlike fluoxetine. (S)-Norfluoxetine is relatively non-toxic and has an excellent therapeutic index. Therefore, the present invention also provides methods of treating the above disorders at rates set forth above for inhibiting serotonin uptake in mammals.

The following experiment was conducted to demonstrate the ability of (S)-norfluoxetine to inhibit the uptake of serotonin as compared with its related enantiomer, racemate, and comparable fluoxetine analogs. This general procedure is set forth by Wong et al., in *Drug Development Research* 6:397–403 (1985).

Male Sprague-Dawley rats (110–150 g) from Harlan Industries (Cumberland, IN) were fed a Purina Chow ad libitum for at least 3 days before being used in the studies. Rats were killed by decapitation. Whole brains were removed and dissected. Cerebral cortex was homogenized in 9 volumes of a medium containing 0.32 M sucrose and 10 mM glucose. Crude synaptosomal preparations were isolated after differential centrifugation at 1,000 g for 10 min. and 17,000 g for 28 min. The final pellets were suspended in the same medium and kept in ice until use within the same day.

Synaptosomal uptake of $^3$H-serotonin ($^3$H-5-hydroxytryptamine, $^3$H-5HT) was determined as follows. Cortical synaptosomes (equivalent to 1 mg of protein) were incubated at 37° C. for 5 min in 1 ml of Krebs-bicarbonate medium containing also 10 mM glucose, 0.1 mM iproniazid, 1 mM ascorbic acid, 0.17 mM EDTA, 50 nM $^3$H-5HT, and appropriate concentrations of test compound. The reaction mixture was immediately diluted with 2 ml of ice-chilled Krebs-bicarbonate buffer and filtered under vacuum with a cell harvester (Brandel, Gaithersburg, Md.). Filters were rinsed twice with approximately 5 ml of ice-chilled 0.9% saline and were transferred to a counting vial containing 10 ml of scintillation fluid (PCS, Amersham, Arlington Heights, IL). Radioactivity was measured by a liquid scintillation spectrophotometer. Accumulation of $^3$H-5HT at 4° C. represented the background and was subtracted from all samples.

The results of the evaluation of (S)-norfluoxetine and related compounds from two side-by-side experiments are set forth below in Table I. In the Table, column 1 identifies the compound evaluated, and column 2 provides the nanomolar (nM) concentration of the test compound needed to inhibit 50% of serotonin (5HT) uptake and is indicated in the Table as the IC$_{50}$. The first experiment employed an older lot of $^3$H-5HT whereas the second experiment employed a new lot of $^3$H-5HT.

TABLE I

| INHIBITION OF 5HT UPTAKE IN VITRO | | |
|---|---|---|
| | 5HT IC$_{50}$ (nM) | |
| Compound | Expt. 1 | Expt. 2 |
| (R,S)-norfluoxetine | 202 | 55.8 |
| (R)-norfluoxetine | 1051 | 484.1 |
| (S)-norfluoxetine | 69 | 29.8 |
| (R,S)-fluoxetine | 79 | 34.4 |
| (R)-fluoxetine | 127 | 39.7 |
| (S)-fluoxetine | 93 | 25.0 |

The compound and salts of the present invention are preferably formulated prior to administration. Therefore, yet another embodiment of the present invention is a pharmaceutical formulation comprising (S)norfluoxetine, or a pharmaceutically acceptable salt thereof, and one or more pharmaceutically acceptable carriers, diluents or excipients therefor. Preferred formulations are those containing either Form 3 or especially Form 1 of (S)-norfluoxetine hydrochloride.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are actual formulations of the drug product.

Formulation 1

Hard gelatin capsules were prepared using the following ingredients:

|  | Quantity (mg/capsule) |
| --- | --- |
| (S)-Norfluoxetine maleate hemihydrate | 1.44 |
| Starch powder | 226.6 |
| Silicone Fluid 350 CS | 2.0 |
| Total | 230.04 mg |

The above ingredients were mixed and filled into hard gelatin capsules in 230.04 mg quantities. Each capsule contained the equivalent of 1 mg of (S)-norfluoxetine (base).

Formulation 2

Twenty milligrams ((S)-Norfluoxetine base equivalents) containing capsules were prepared using the following ingredients:

|  | Quantity (mg/capsule) |
| --- | --- |
| (S)-Norfluoxetine maleate hemihydrate | 28.78 |
| Starch powder | 199.2 |
| Silicone Fluid 350 CS | 2.00 |
| Total | 229.98 mg |

The above ingredients were mixed and filled into hard gelatin capsules in 229.98 mg quantities.

The following formulation examples are illustrative only and are not intended to limit the scope of the invention in any way.

Formulation 3

Hard gelatin capsules are prepared using the following ingredients:

|  | Quantity (mg/capsule) |
| --- | --- |
| (S)-Norfluoxetine hydrochloride Form 1 | 250 |
| starch, dried | 200 |
| magnesium stearate | 10 |
| Total | 460 mg |

The above ingredients are mixed and filled into hard gelatin capsules in 460 mg quantities.

Formulation 4

A tablet is prepared using the ingredients below:

|  | Quantity (mg/tablet) |
| --- | --- |
| (S)-Norfluoxetine hydrochloride Form 1 | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 5

An aerosol solution is prepared containing the following components:

|  | Weight % |
| --- | --- |
| (S)-Norfluoxetine oxalate | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

Formulation 6

Tablets each containing 60 mg of active ingredient are made as follows:

| (S)-Norfluoxetine phosphate | 60 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 7

Capsules each containing 80 mg of medicament are made as follows:

| | |
|---|---|
| (S)-Norfluoxetine tartrate | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 8

Suppositories each containing 225 mg of active ingredient may be made as follows:

| | |
|---|---|
| (S)-Norfluoxetine | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 9

Suspensions each containing 50 mg of medicament per 5 ml dose are made as follows:

| | |
|---|---|
| (S)-Norfluoxetine napsylate | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 10

An intravenous formulation may be prepared as follows:

| | |
|---|---|
| (S)-norfluoxetine hydrochloride | 100 mg |
| isotonic saline | 1000 ml |

The solution of the above ingredients is administered intravenously at a rate of 1 ml per minute to a subject suffering from depression.

We claim:

1. A method for inhibiting serotonin uptake in mammals which comprises administering to a mammal requiring increased neurotransmission of serotonin an effective amount of (S)-norfluoxetine or a salt or solvate thereof substantially free of (R)-norfluoxetine.

2. A method of treating depression in humans comprising administering to a human suffering from depression an effective antidepressant dose of (S)-norfluoxetine or a salt or solvate thereof substantially free of (R)-norfluoxetine.

3. A method of treating obesity in humans comprising administering to a human suffering from obesity an effective anti-obesity dose of (S)-norfluoxetine or a salt or solvate thereof substantially free of (R)-norfluoxetine.

4. A method of treating bulimia in humans comprising administering to a human suffering from bulimia an effective anti-bulimic dose of (S)-norfluoxetine or a salt or solvate thereof substantially free of (R)-norfluoxetine.

5. A method of treating obsessive-compulsive disorders in humans comprising administering to a human suffering from an obsessive-compulsive disorder an effective amount of (S)-norfluoxetine or a salt or solvate thereof substantially free of (R)-norfluoxetine.

6. The method of claim 1 employing (S)-norfluoxetine.

7. The method of claim 1 employing (S)-norfluoxetine hydrochloride.

8. The method of claim 1 employing (S)-norfluoxetine maleate or a solvate thereof.

9. The method of claim 8 employing (S)-norfluoxetine maleate hemihydrate.

10. The method of claim 2 employing (S)-norfluoxetine.

11. The method of claim 2 employing (S)-norfluoxetine hydrochloride.

12. The method of claim 2 employing (S)-norfluoxetine maleate or a solvate thereof.

13. The method of claim 12 employing (S)-norfluoxetine maleate hemihydrate.

14. The method of claim 3 employing (S)-norfluoxetine.

15. The method of claim 3 employing (S)-norfluoxetine hydrochloride.

16. The method of claim 3 employing (S)-norfluoxetine maleate or a solvate thereof.

17. The method of claim 16 employing (S)-norfluoxetine maleate hemihydrate.

18. The method of claim 4 employing (S)norfluoxetine.

19. The method of claim 4 employing (S)norfluoxetine hydrochloride.

20. The method of claim 4 employing (S)norfluoxetine maleate or a solvate thereof.

21. The method of claim 20 employing (S)norfluoxetine maleate hemihydrate.

22. The method of claim 5 employing (S)norfluoxetine.

23. The method of claim 5 employing (S)norfluoxetine hydrochloride.

24. The method of claim 5 employing (S)norfluoxetine maleate or a solvate thereof.

25. The method of claim 24 employing (S)norfluoxetine maleate hemihydrate.

* * * * *

UNITED STATES PATENT AND TRADEMARK OFFICE
CERTIFICATE OF CORRECTION

PATENT NO. : 5,250,571

DATED : October 5, 1993

INVENTOR(S) : R. W. Fuller et al.

It is certified that an error appears in the above-identified patent and that said Letters Patent is hereby corrected as shown below:

Title page, item [75],
The inventors of patent 5,250,571 read "...Ray W. Fuller; David Mitchell, both of Indianapolis; David W. Robertson, Greenwood; Gregory A. Stephenson, Anderson; David T. Wong, Indianapolis, all of Ind...." should read --...Ray W. Fuller, Indianapolis; David W. Robertson, Greenwood; David T. Wong, Indianapolis, all of Ind....--

Signed and Sealed this

Twentieth Day of September, 1994

Attest:

BRUCE LEHMAN

Attesting Officer

Commissioner of Patents and Trademarks